(12) United States Patent
Manera et al.

(10) Patent No.: US 7,070,581 B2
(45) Date of Patent: Jul. 4, 2006

(54) DISPENSER FOR MEDICAMENTS AND METHOD AND APPARATUS FOR MAKING SAME

(75) Inventors: David A. Manera, Petersburg, NJ (US); John D. Buehler, Bridgeton, NJ (US)

(73) Assignee: Comar, Inc., Buena, NJ (US)

(*) Notice: Subject to any disclaimer, the term of this patent is extended or adjusted under 35 U.S.C. 154(b) by 80 days.

(21) Appl. No.: 10/407,360

(22) Filed: Apr. 4, 2003

(65) Prior Publication Data

US 2004/0010238 A1 Jan. 15, 2004

Related U.S. Application Data

(60) Provisional application No. 60/370,203, filed on Apr. 5, 2002.

(51) Int. Cl.
*A61M 5/315* (2006.01)

(52) U.S. Cl. ..................................... 604/218
(58) Field of Classification Search ............. 604/187, 604/218, 110, 220, 222, 227, 230
See application file for complete search history.

(56) References Cited

U.S. PATENT DOCUMENTS

| | | | | |
|---|---|---|---|---|
| 4,201,209 A | * | 5/1980 | LeVeen et al. | 604/218 |
| 4,704,105 A | * | 11/1987 | Adorjan et al. | 604/222 |
| 5,037,382 A | * | 8/1991 | Kvorning et al. | 604/220 |
| 5,411,489 A | | 5/1995 | Pagay et al. | |
| 5,735,825 A | | 4/1998 | Stevens et al. | |
| 5,935,104 A | | 8/1999 | Janek et al. | |
| 6,224,577 B1 | | 5/2001 | Dedola et al. | |

* cited by examiner

Primary Examiner—Michael J. Hayes
Assistant Examiner—Mark K Han
(74) Attorney, Agent, or Firm—Eugene E. Renz, Jr.

(57) ABSTRACT

A dispenser assembly for liquid products comprising an elongated, generally cylindrical barrel of a predetermined internal cross-sectional diameter having a discharge opening at one end and open at its opposite end, an elongated, generally cylindrical hollow plunger having an outer diameter less than the barrel internal diameter and a circumferentially extending axially directed sealing lip adjacent the tip portion having an outer diameter greater than the internal diameter of the barrel in the relaxed state to thereby flex the lip inwardly against its bias and providing the sole sliding contact between the plunger and barrel when the plunger and barrel are actuated axially relative to one another.

3 Claims, 20 Drawing Sheets

DISPENSER FOR MEDICAMENTS AND METHOD AND APPARATUS FOR MAKING SAME

This application claims the benefit of U.S. Provisional Application No. 60/370,203 filed Apr. 5, 2002.

FIELD OF THE INVENTION

The present invention relates to a dispenser assemblies for dispensing liquid products and in particular to dispensers of the type useful in administering medicaments, such as liquid aspirin to children and to a method and apparatus for making a plunger part of the dispenser.

BACKGROUND OF THE INVENTION

The prior art as exemplified by the patents listed below show syringe assemblies for dispensing injectable medicaments which generally comprise an elongated, hollow barrel having luer-type fitting at the discharge end to mount a needle or cannula and a plunger rod which mounts a plunger usually made of rubber has radially outwardly projecting lugs or ribs which engage the barrel interior side wall during activation of the plunger rod axially in the barrel during filling of the syringe or activation of the plunger in an injection cycle. Even though these syringes are generally suitable for the purposes, it is been found that in some instances they are relatively expensive to manufacture by reason of the tolerances required to obtain the desired seal between the plunger ribs and the barrel and to prevent bypass or leakage of the medication during an injection stroke and the desired easy movement of the plunger when activating the same. It has been found that even where tolerances are controlled, leakage and ease of activation of the plunger are problematic.

REFERENCE PATENTS

BRAITHWAITE
TITLE: SYRINGES
U.S. Pat. No. 5,066,280
DATE OF PATENT: NOV. 19, 1991
LINNEBJERG
TITLE: PRELOADABLE SYRINGE FOR AUTOMATED DISPENSING DEVICE
U.S. Pat. No. 5,928,202
DATE OF PATENT: JUL. 27, 1999
DEDOLA et al.
TITLE: SYRINGES AND PLUNGERS FOR USE THEREIN
U.S. Pat. No. 6,224,577
DATE OF PATENT: MAY 1, 2001
STEVENS et al.
TITLE: SYRINGE PLUNGER TIP
U.S. Pat. No. 5,735,825
DATE OF PATENT: APR. 7, 1998
SOMERS
TITLE: SAFETY SYRINGE
U.S. Pat. No. 6,342,045
DATE OF PATENT: JAN. 29, 2002
KOLBERG et al.
TITLE: PREFILLED, STERILIZED SYRINGE WITH A NEW AND IMPROVED PLUG
U.S. Pat. No. 6,142,977
DATE OF PATENT: NOV. 7, 2000
DURÄNZAMPA et al.
TITLE: AUTO-NON-REUSABLE SYRINGE-NEEDLE SYSTEM FOR INJECTIONS FOR A UNIQUE USE
U.S. Pat. No. 5,034,002
DATE OF PATENT: JUL. 23, 1991
GROSS
TITLE: LOW FRICTION SYRINGE
U.S. Pat. No. 5,397,313
DATE OF PATENT: MAR. 14, 1995

SUMMARY OF THE INVENTION

With the foregoing in mind, it is an object of the present invention to provide an oral dose dispenser for use in administering medicaments, such as liquid aspirin to children which is characterized by novel features of construction and arrangement providing an effective seal between the plunger and the barrel and is easy to activate when filling and administering medicaments and which can be manufactured by a unique molding process easily and economically. In the preferred embodiment of the invention, the plunger has a unique and distinctive tip configuration including a circumferentially extending axially directed sealing or wiper lip which projects outwardly at a predetermined lead angle of approximately ten degrees (10°) to the axis of hollow tubular plunger in the relaxed state. By this construction, the sealing or wiper lip provide essentially a circumferentially extending single point of contact with the barrel bore surface and thus, the present invention combines the advantages of the prior art rubber and plastic plungers since it is economical to manufacture and functions properly over a widertolerance range. In other words, the plunger-barrel design of the present invention has the desired "feel" for ease of actuation over a wide range of tolerances. The plunger easily rides in the barrel and ensures a clean and in depth dispensing of the product through the discharge tip in the barrel.

In a preferred embodiment, the plunger and barrel are made of dissimilar materials to provide greater lubricity between the plunger and the barrel which contributes to easy movement and which prevents galling. The barrel is preferably made of a clear plastic, such as polypropylene, and the plunger is made of a high-density polyethylene and is of an opaque color so that the contrast provided by the sealing lip arrangement and the plunger tip makes it easy for the user to determine the fill height when filling the dispenser as explained in more detail hereafter. Typically, these assemblies comprising a rubber plunger and a plastic or glass barrel are not tolerance sensitive since an external lubricant is usually applied to the plunger to facilitate relatively easy movement of the plunger in the barrel. With these plural-part assemblies, however, the plunger can easily disassemble from the plunger rod and present a choking hazard to a child. Plastic plungers are also known and are less expensive to manufacture but generally present tolerance problems. For example, it has been found that small tolerance variations from one assembly to the next can make a large change in how smoothly the plunger rides in the barrel when activated.

Further as explained, the molding process of the present invention is greatly simplified because only mold components which act in two directions are required to form the plunger configuration with the flexible axially extending sealing lip. The prior art does not disclose a plunger and barrel combination where the plunger and barrel are essentially elongated, hollow tubular members and the plunger has a sealing lip formed integrally therewith providing the only contact element with the barrel during activation to fill or discharge liquid products, such as medicaments.

BRIEF DESCRIPTION OF THE DRAWINGS

These and other objects of the present invention and various features and details of the operation and construction thereof are hereinafter more fully set forth with reference to the accompanying drawings wherein;

FIG. 9a is a transverse sectional view similar to FIG. 8a with the plunger fully withdrawn;

FIG. 9b is an enlarged view showing the relationship of the parts when the plunger and barrel are in the position shown in FIG. 9a;

DESCRIPTION OF PREFERRED EMBODIMENTS

Figure 1:
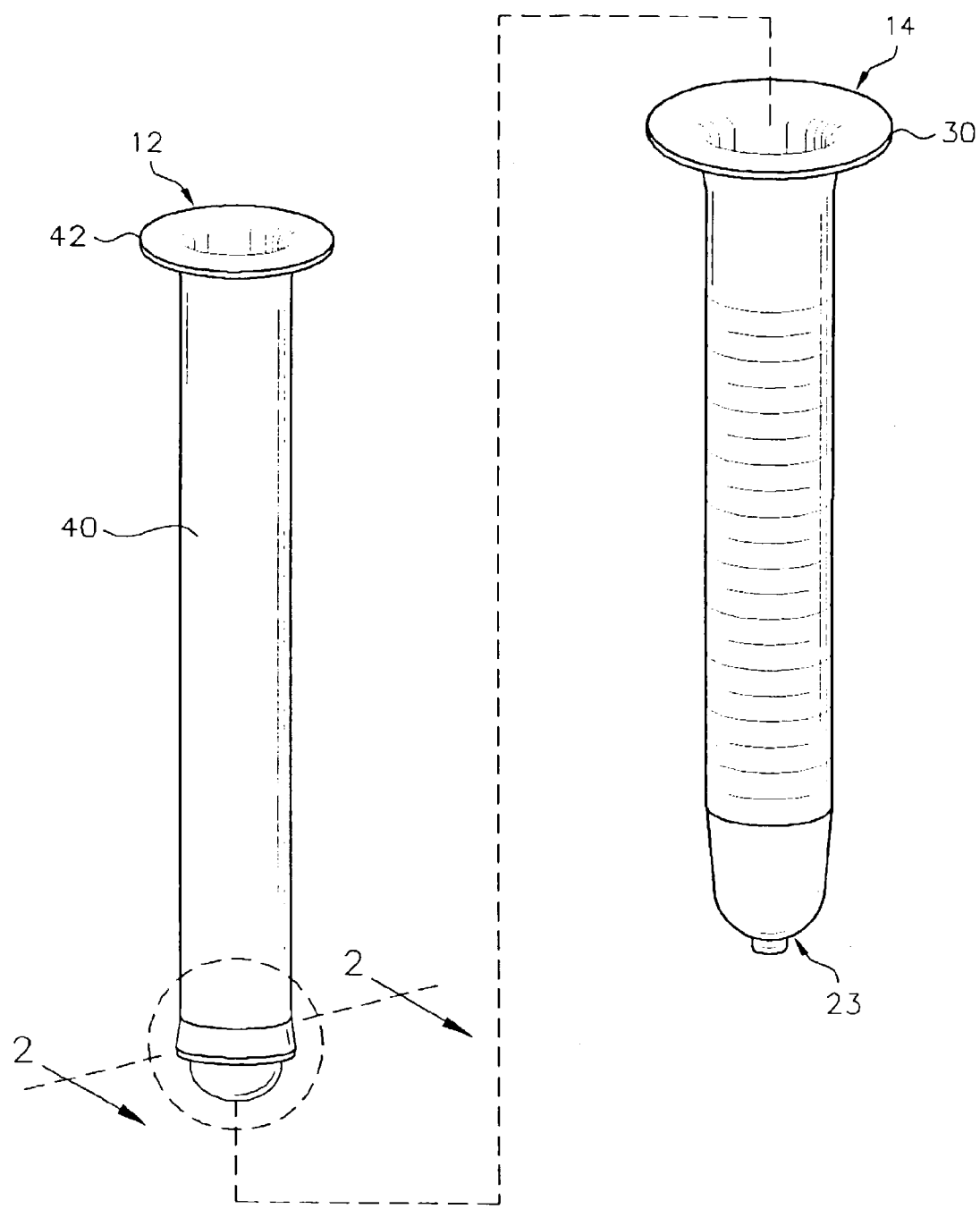
FIG. 1 is a perspective view of a plunger and barrel of an oral dispensing assembly in accordance with the present invention particularly adapted for administering medicaments to children.
Figure 2:
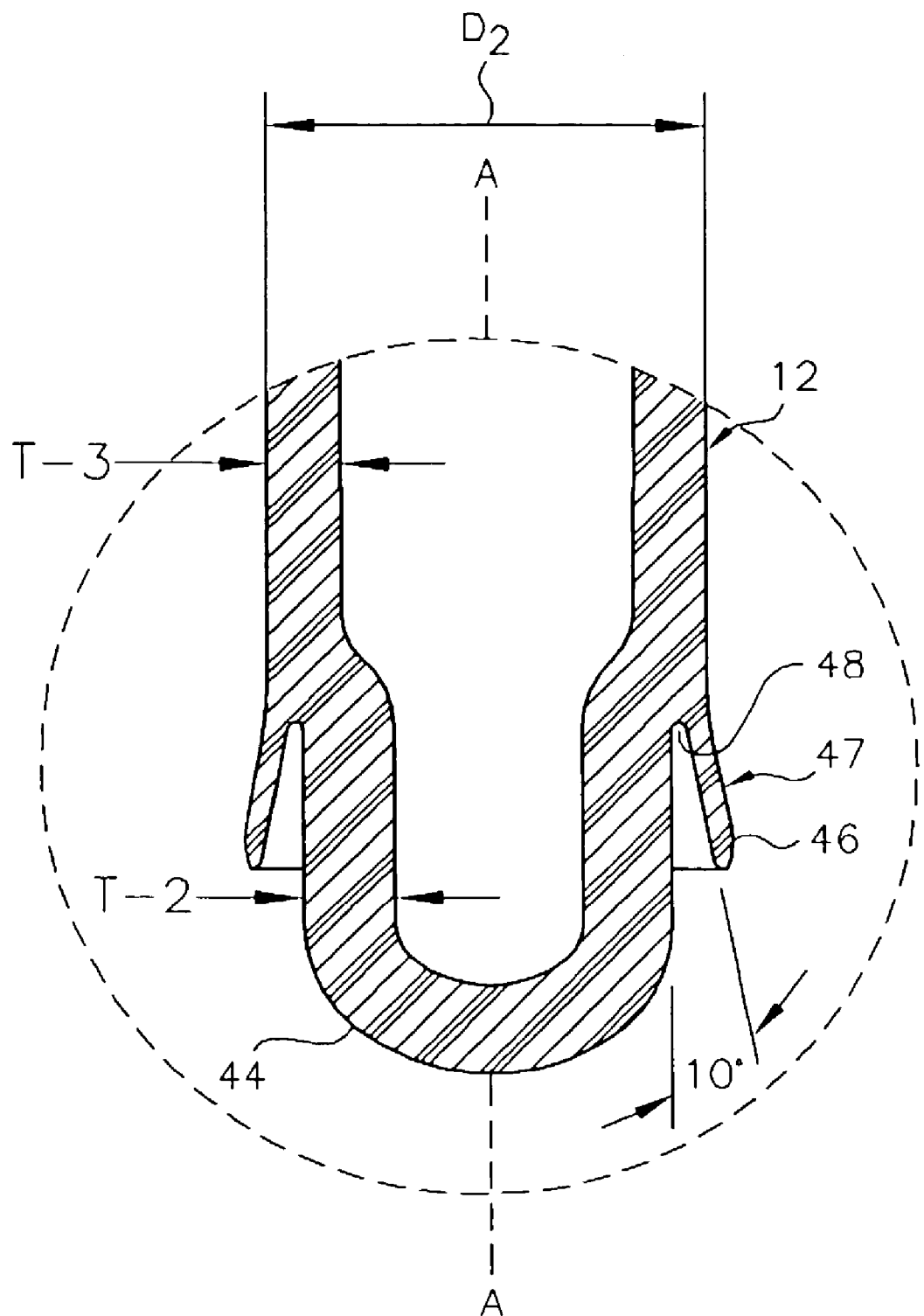
FIG. 2 is an enlarged fragmentary sectional view taken on lines 2—2 of FIG. 1 showing the plunger tip configuration.

Referring now to the drawings and particularly to FIG. 1 thereof, there is shown an oral dispensing assembly in accordance with the present invention generally designated by the numeral (10), as shown the assembly comprises an elongated plunger (12) which fits in and slides in an elongated, hollow barrel (14).

Figures 5A, 5B:
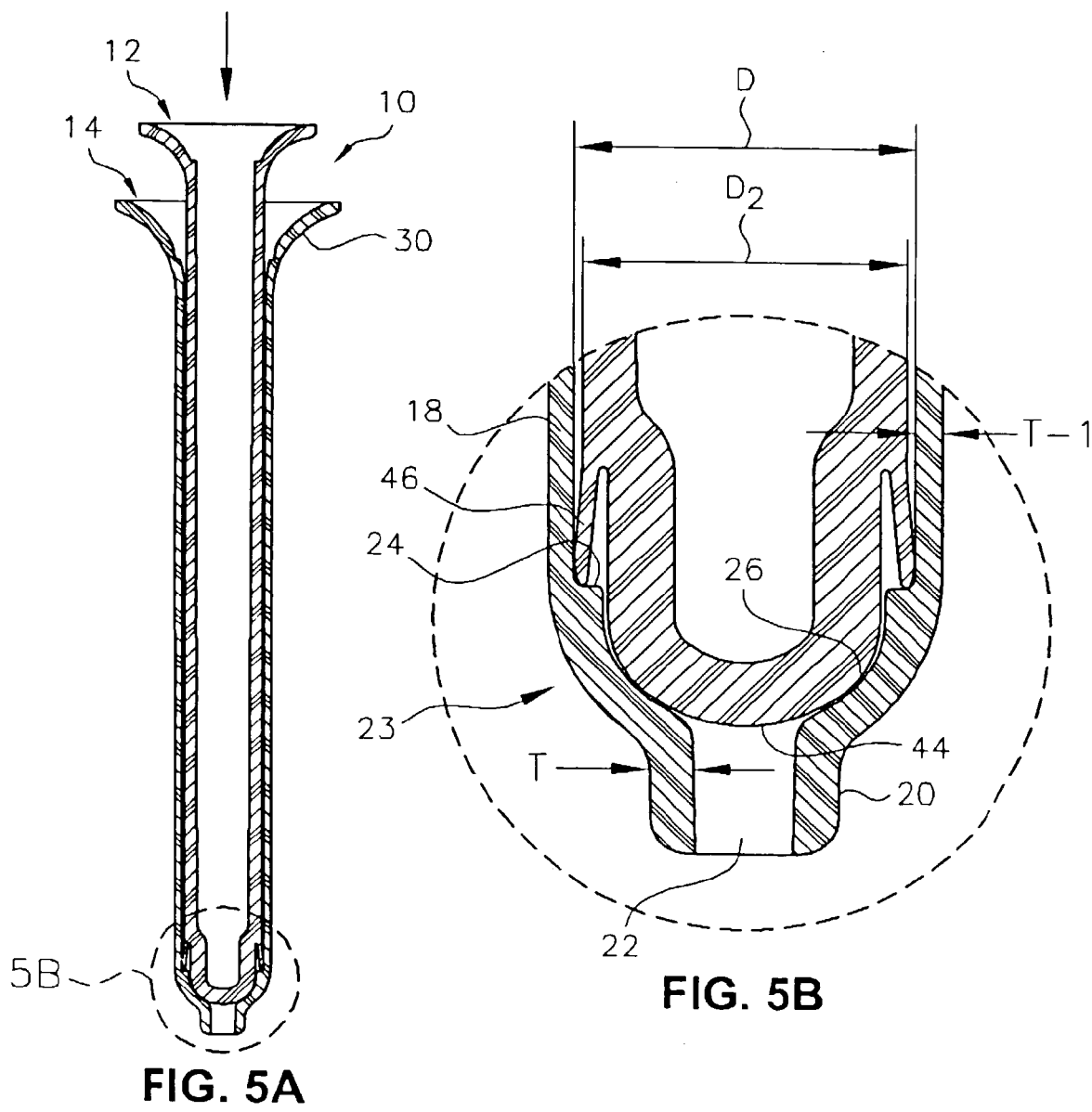
FIG. 5a is a transverse sectional view showing the plunger fully bottomed out and the contents completely dispensed.
FIG. 5b is an enlarged fragmentary sectional view of the portion circled in FIG. 5a identified by the reference numeral 5b.
Figure 6:
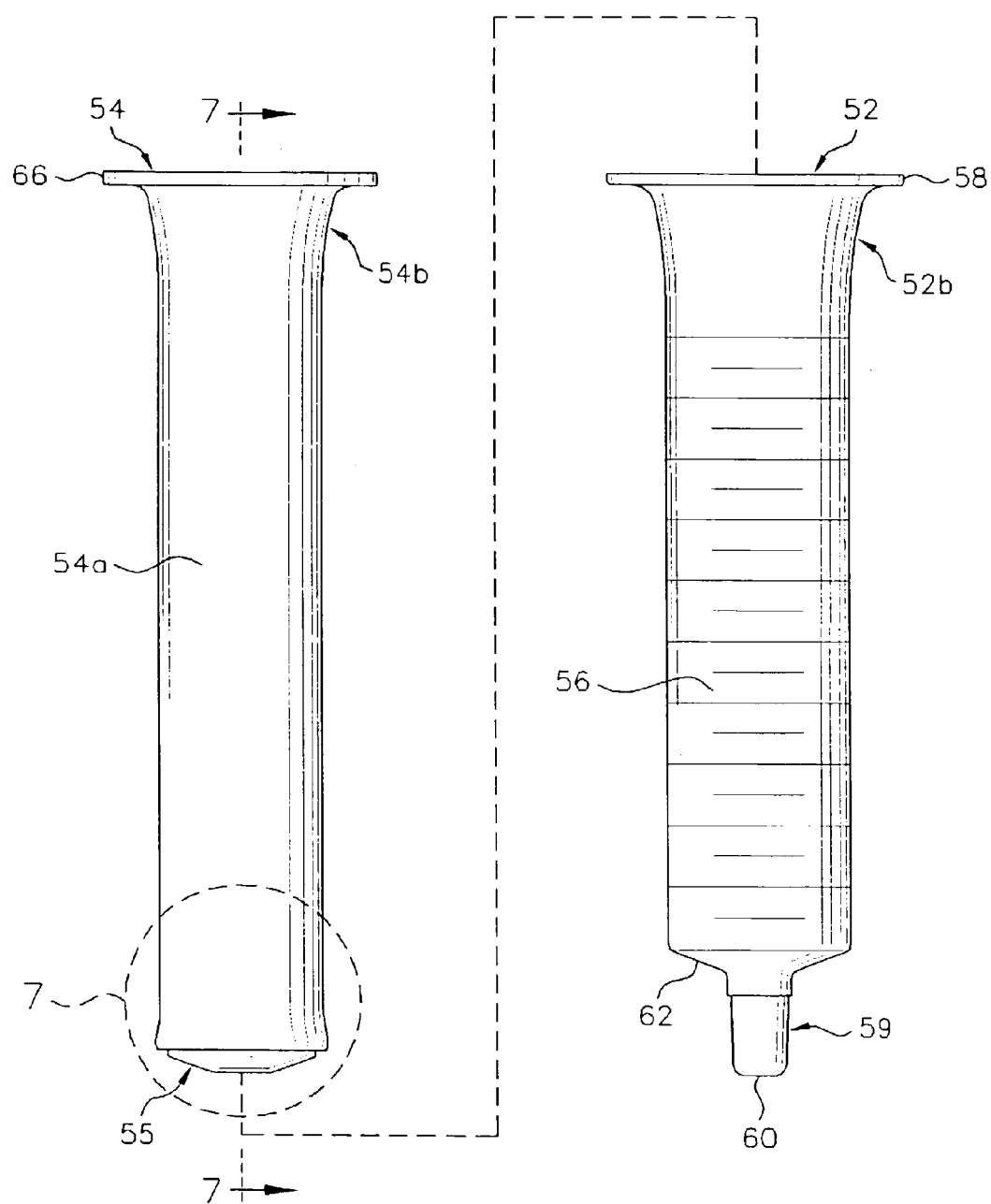
FIG. 6 is an exploded side elevational view of another embodiment of oral dispensing assembly in accordance with the present invention.
Figure 7:
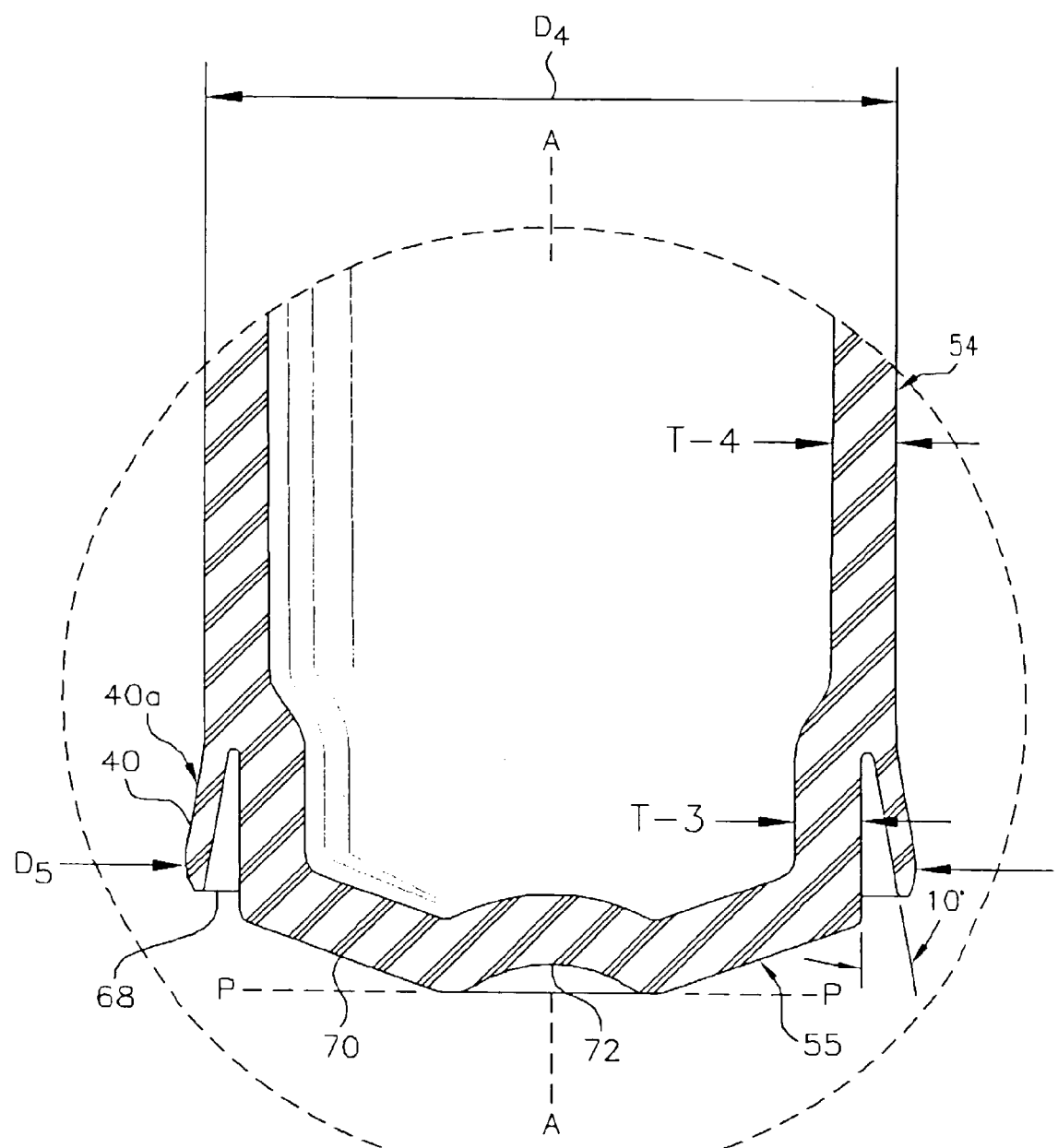
FIG. 7 is an enlarged exploded view of the tip of the plunger circled in FIG. 6 and identified by the reference numeral 7.
Figures 8A, 8B:
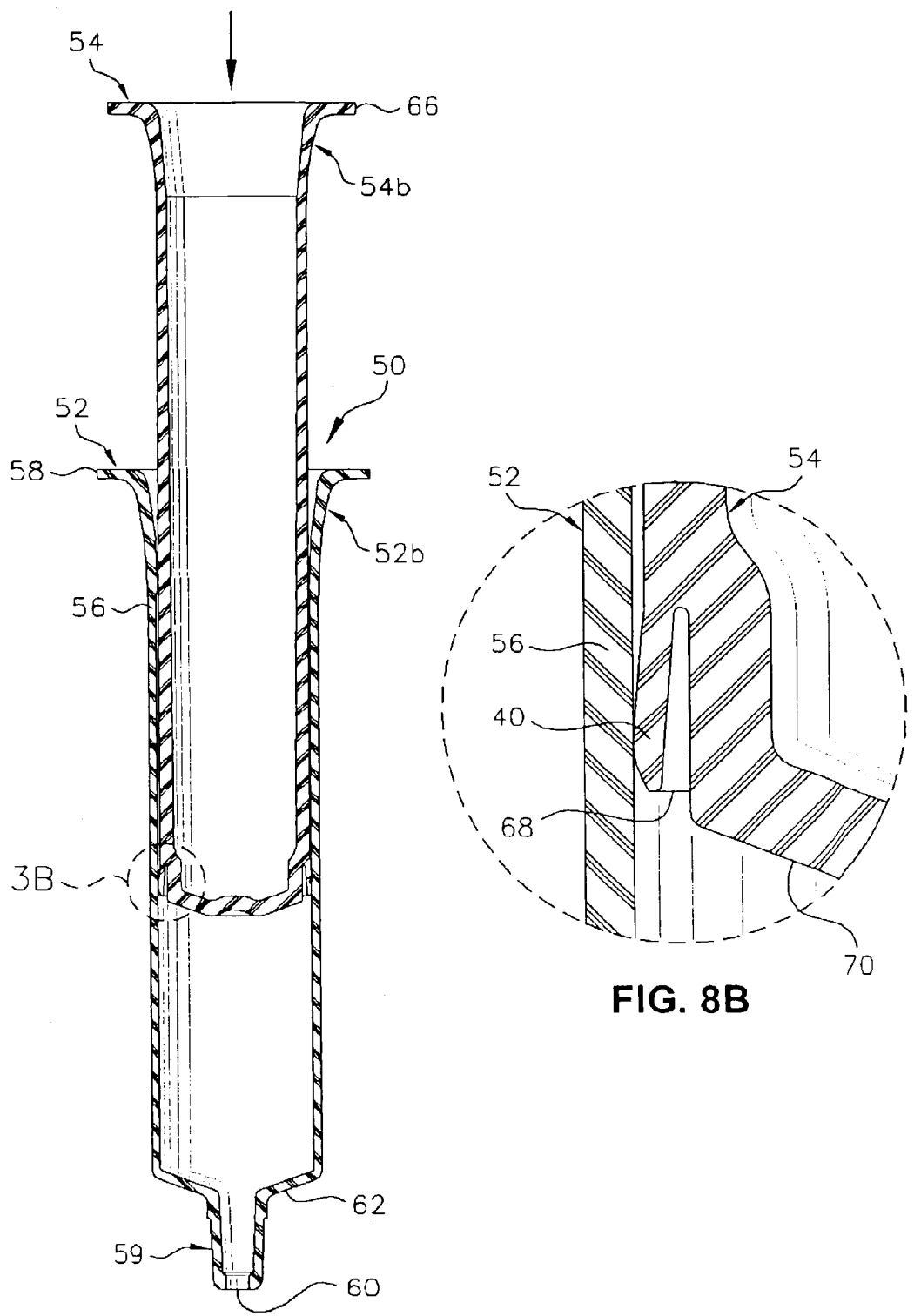
FIG. 8a is a transverse sectional view showing the plunger assembled in the barrel.
FIG. 8b is an enlarged fragmentary view of the portioned circled in FIG. 8a and referenced by the numeral 8b.
Figures 9A, 9B:
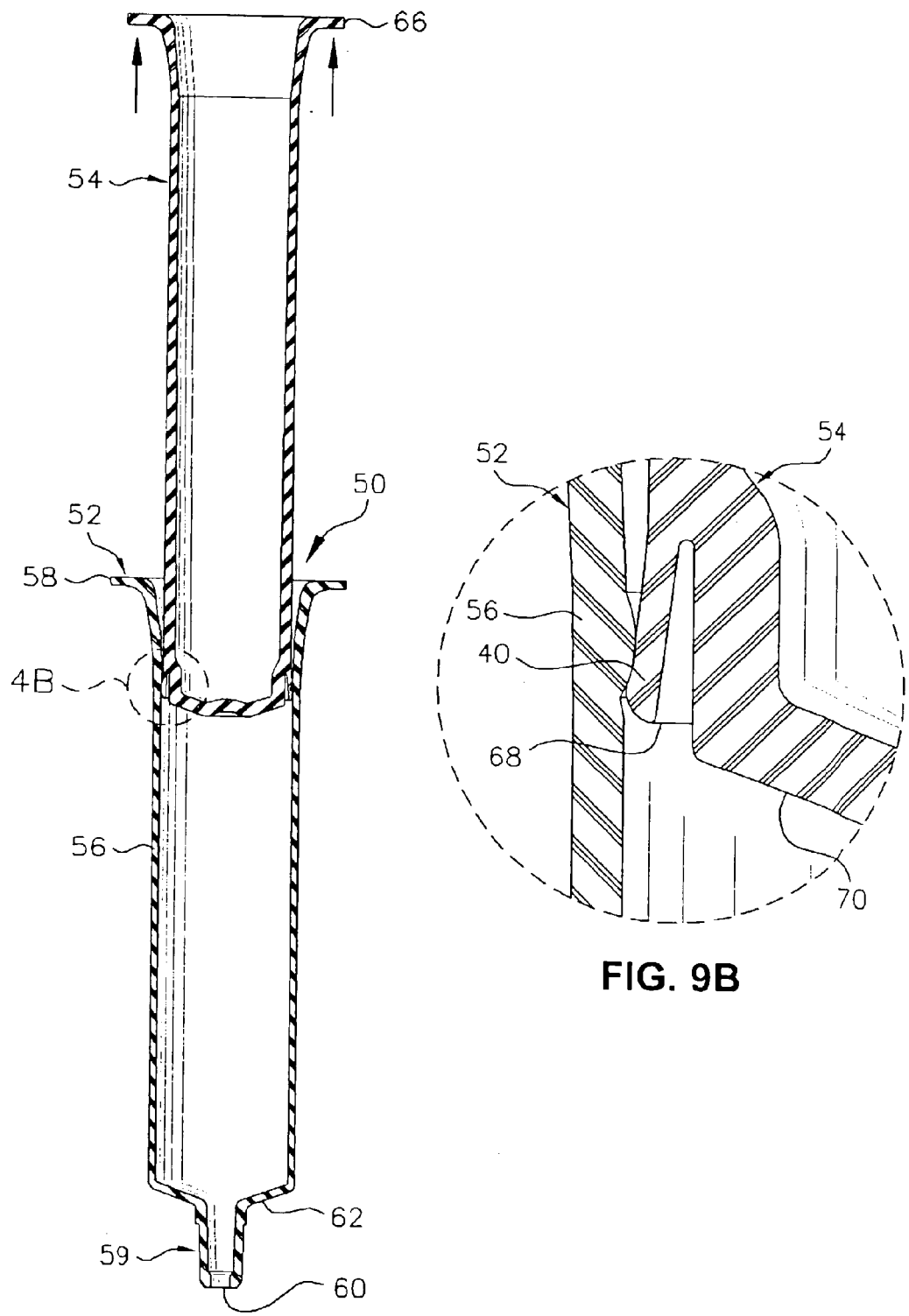
Figure 9C:
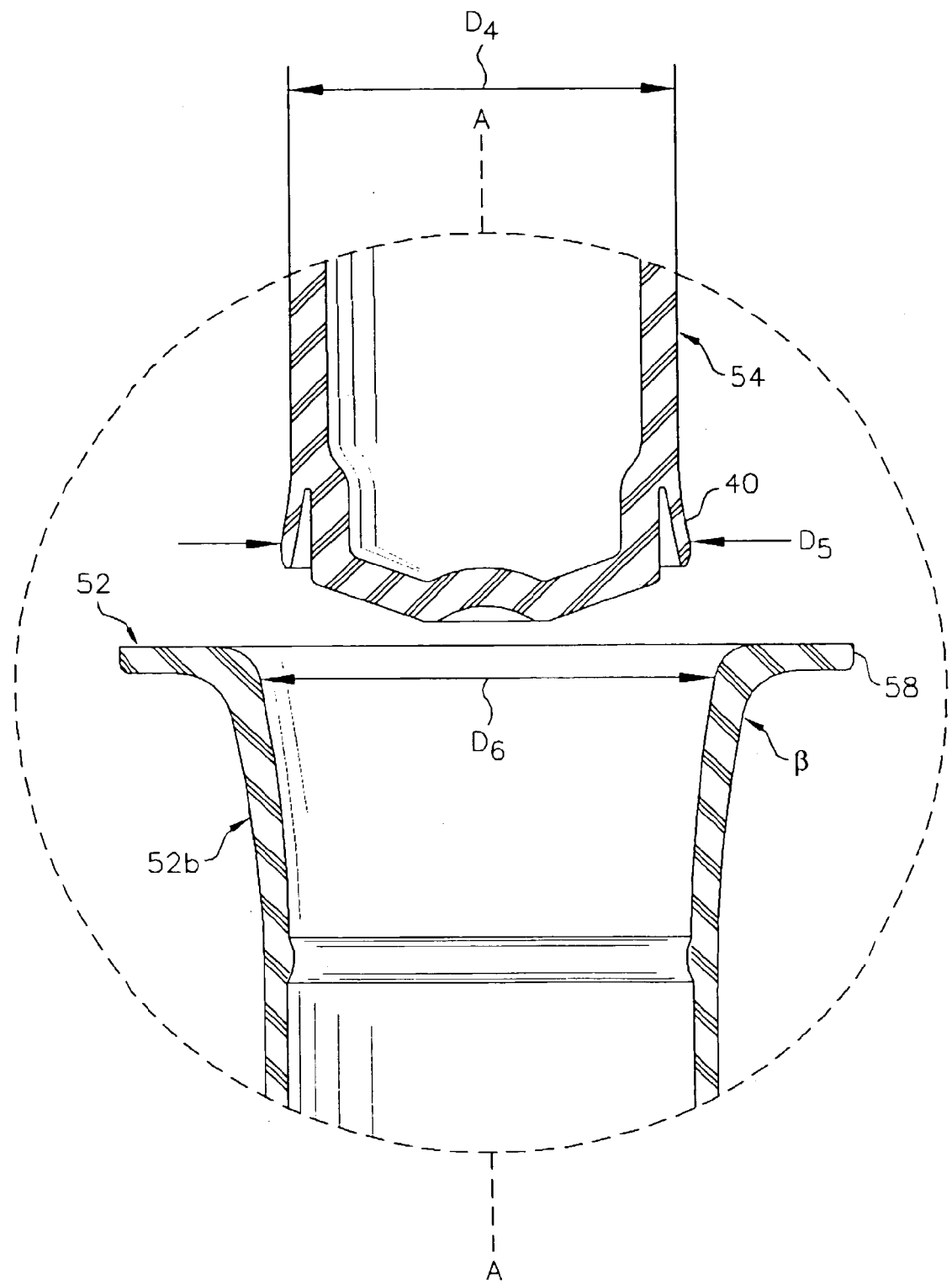
FIG. 9c is an exploded, enlarged fragmentary sectional view of the plunger tip and entrance end of the barrel.

The barrel (14) as best illustrated in FIGS. 5a and 5b is made of a plastic material and comprises a generally cylindrical, elongated side wall (18) having a bore ($18^a$) of generally uniform diameter D for its length having a tip (20) at one end with a discharge opening (22) through which medicament products are dispensed. The tip end (20) as illustrated in 5b is of a greater cross section T than the barrel side wall thickness T-1 to define a circumferentially extending ledge (24). The interior of the tip (20) is shaped to define a spherical seat (26). The barrel (14) is outwardly flared at its opposing upper terminal end as at (30) and has a pair of circumferentially extending spaced protrusions (34) and (36) in the region where the cylindrical body portion (18) of the barrel merge with the outwardly flared finger grip portion (30).

Figure 3A:
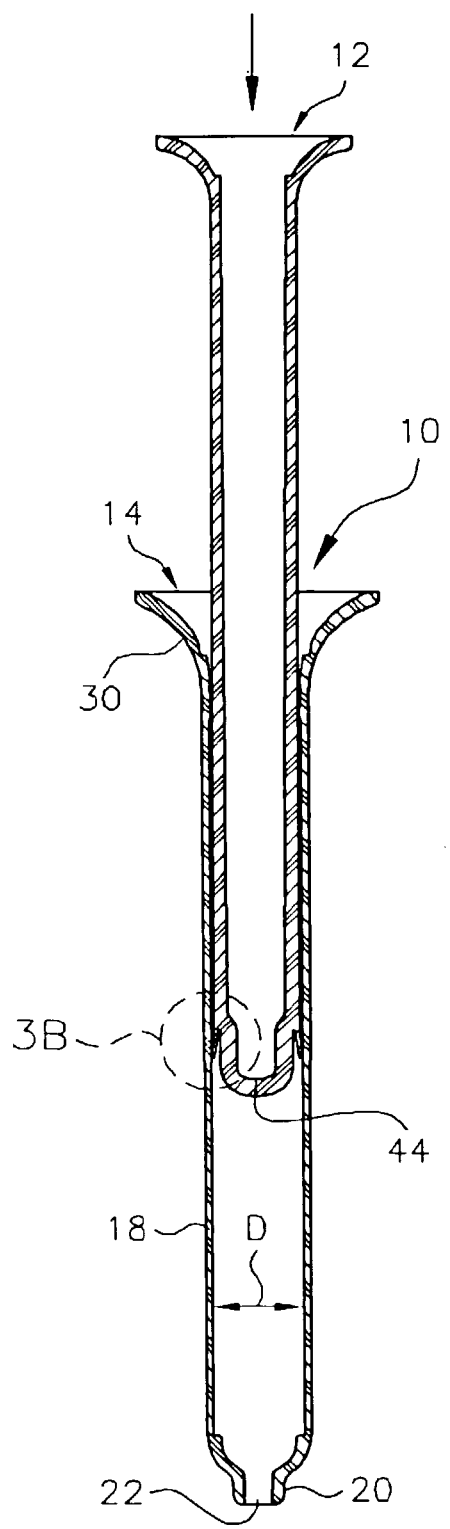
FIG. 3a is a transverse sectional view of the plunger and barrel assembled.
Figure 3B:
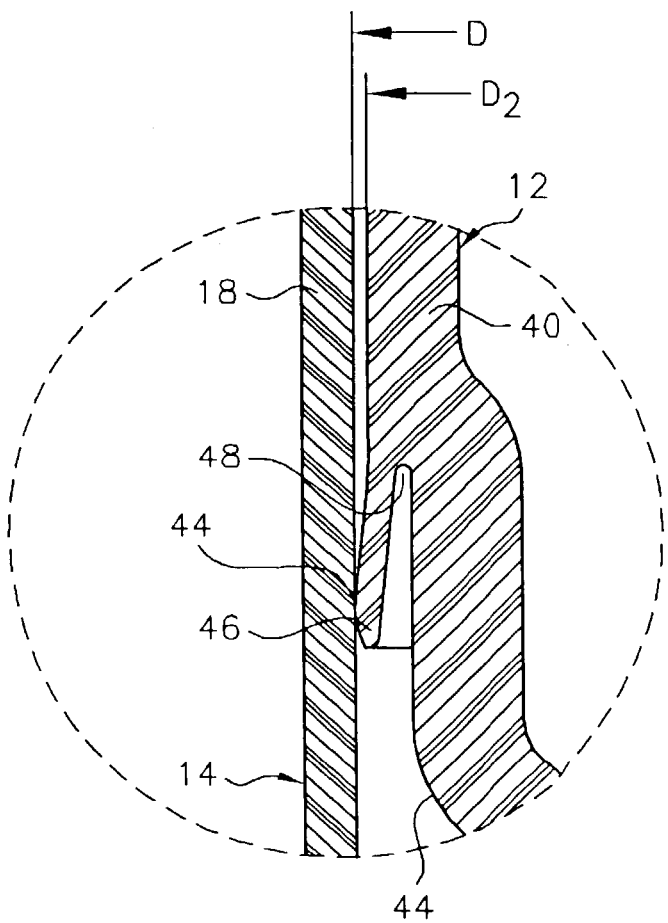
FIG. 3b is an enlarged sectional view showing the sealing lip engaging the inside of the barrel.
Figures 4A, 4B:
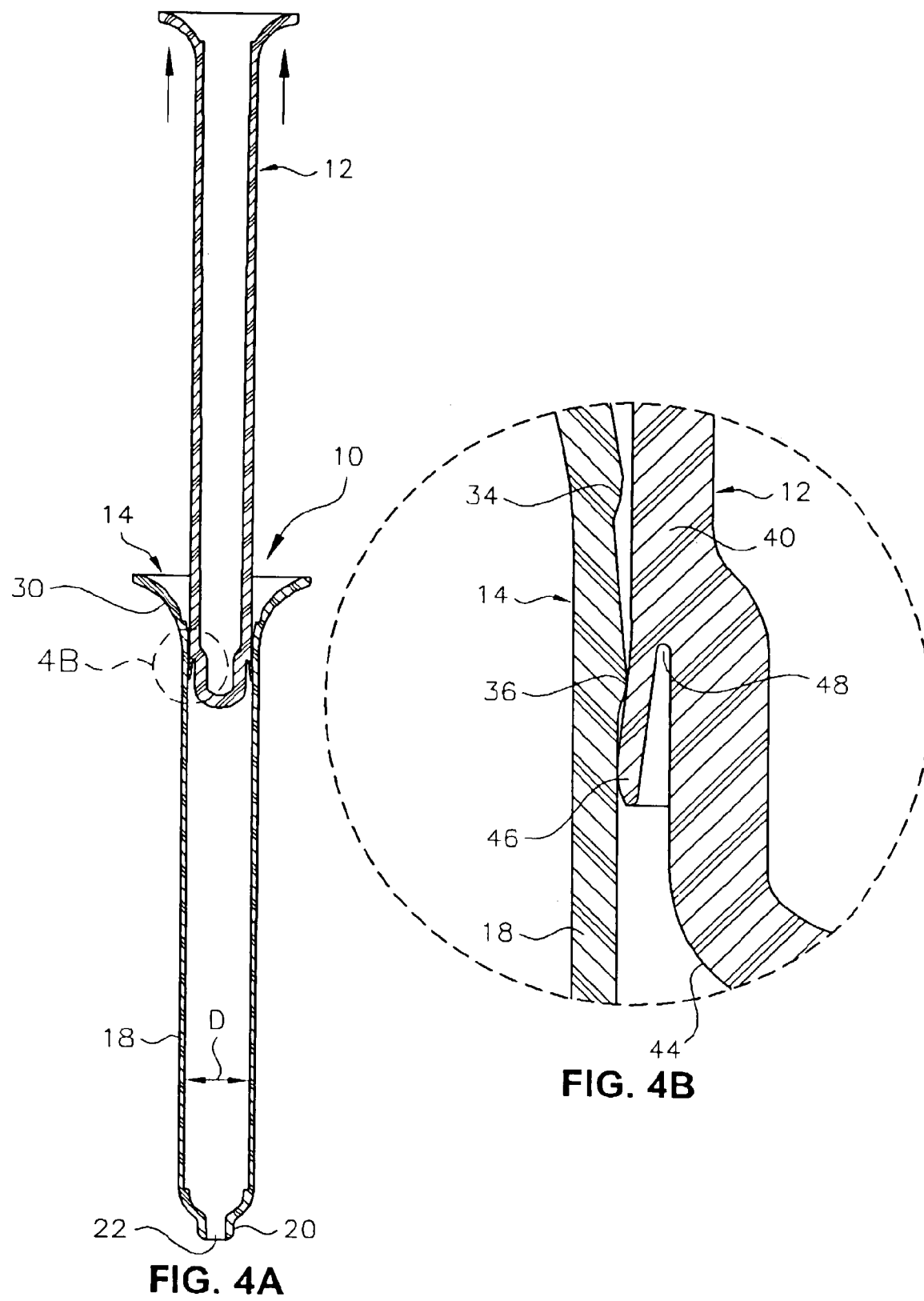
FIG. 4a is a transverse sectional view similar to FIG. 3a showing the plunger at the upper end of its retract stroke.
FIG. 4b is an enlarged fragmentary sectional view of the portion circled in FIG. 4a and identified by numeral 4b.

The plunger (12) is also made of plastic and has an elongated generally cylindrical elongated body portion (40) which is outwardly flared to define a flange (42) at its upper end serving as a finger grip portion for activation of the plunger in the barrel. The plunger (12) as illustrated has a bulbous nose (44) at its tip end. The nose portion (44) is offset from the side wall (40) as shown at 5b and has a cross sectional thickness T-2 slightly greater than the cross section T-3 of cylindrical body portion of the plunger. A downwardly and slightly outwardly biased sealing lip (46) projects axially from the lower end of the plunger at the juncture (48) of the cylindrical body portion (40) and nose section (44) and has a slightly beveled outer edge (47) confronting the inner wall of the barrel as shown in FIG. 3b. The tip of the sealing lip (46) is spaced upwardly from the nose portion so that when the plunger is fully seated the sealing lip (46) engages the ledge (24) when the nose portion engages the spherical seat. The sealing lip (40) projects outwardly at an angle alpha ($\alpha$) of about ten degrees (10°) to the longitudinal axis A—A of the plunger.

The inside diameter D of the barrel is slightly greater than the external diameter $D_2$ of the plunger to provide a slight clearance C between the parts so that the flexible sealing lip (46) is essentially the sole contact when activating the plunger to fill or discharge product.

The barrel (14) is preferably made of polypropylene and the plunger (12) is preferably made of a high-density polyethylene. It has been found that this combination of materials and the specific configuration facilitate easy sliding of the parts relative to one another and does not require the close molding tolerances that prior art syringes require. Further the plunger (12) is easy and economical to manufacture by reason of the simple mold design which does not require side action components. The tooling therefore is relatively simple and does not require the complex tooling which prior art syringe assemblies require. The tooling can accommodate more cavities for a given tonnage and is therefore very economical and cost saving.

Consider briefly the use of an oral dosing assembly in accordance with the present invention. With the plunger (12) fully seated in the barrel (14) as shown in FIG. 5a, the user simply inserts the barrel and plunger into a container for the medicament to be dispensed the user then pulls the plunger (12) upwardly to draw the desired quantity into the barrel. The barrel is graduated in markings to aid in the filling process. The user then simply inserts the tip end into the mouth of a child and pushes the barrel forwardly to dispense product. It is noted that when the barrel is drawn to its outer-limit position, the sealing lip (40) engages in one of the protrusions signaling the user not to withdraw the plunger any further.

There is shown in FIG. 7-10 inclusive another embodiment of dispenser assembly in accordance with the present invention generally designated by the numeral (50) which comprises an elongated, hollow barrel (52) and a plunger (54) slidably mounted in the barrel (52). The barrel (52) as illustrated has an elongated, generally cylindrical body portion (56) terminating at its upper end in radially outwardly directed circumferentially extending flange (58) providing a finger grip for the user. The tip (59) has a discharge opening (60) and is connected to the side wall (56) by a downwardly flared conical connecting wall (62).

Figures 10A, 10B:
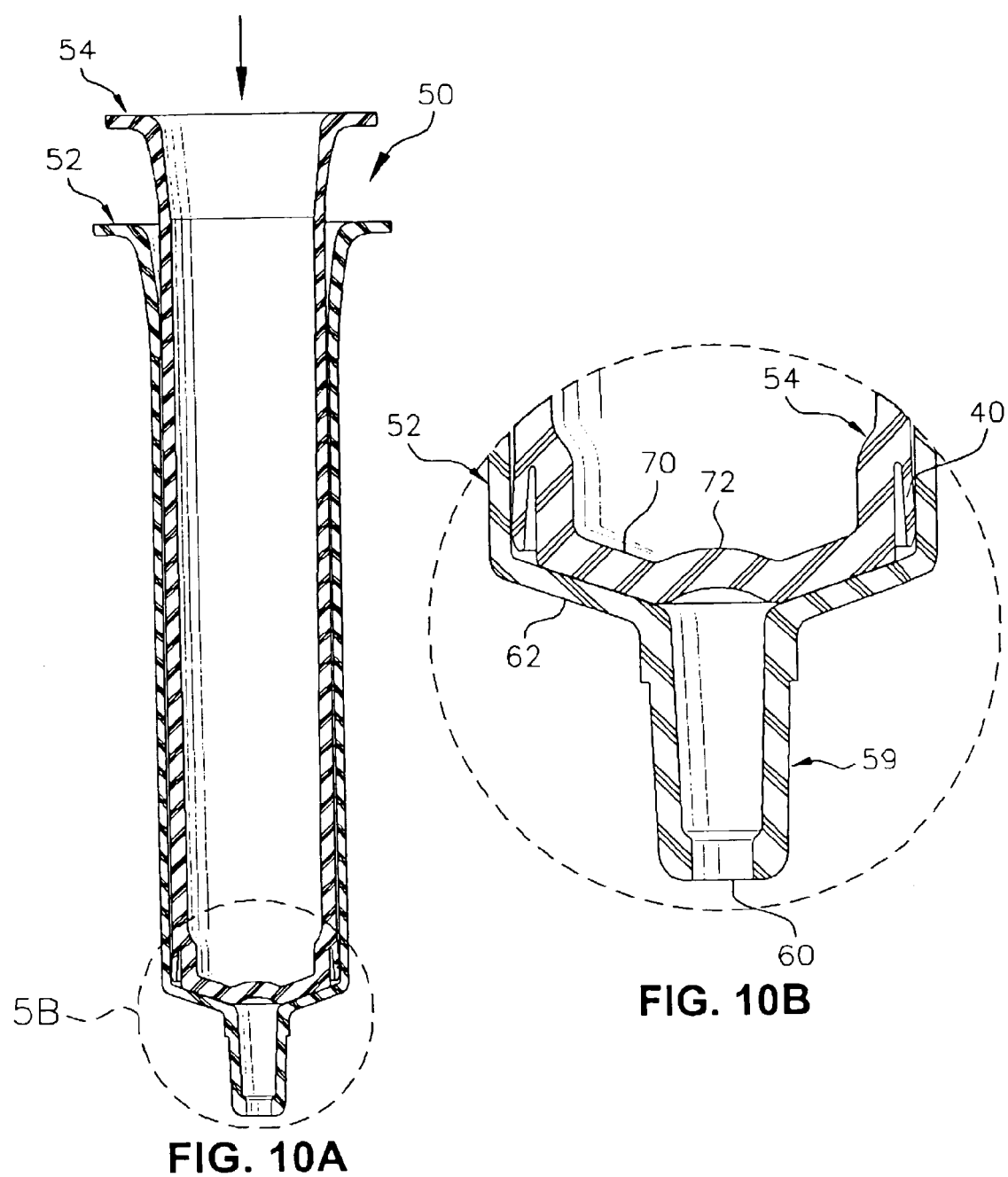
FIG. 10a is a transverse sectional view similar to FIGS. 8a and 9a where the plunger is fully bottomed out in the barrel during a discharge stroke.
FIG. 10b is an enlarged fragmentary sectional view of the portion circled in FIG. 10a and identified by the reference numeral 10b.

The plunger (54) has an elongated body portion ($54^a$) having a generally uniform diameter ($D_4$) which has an outwardly flared section ($54^b$) at its upper open end and terminates in a circumferentially extending radially outwardly directed flange (66) serving as a finger grip for the user to activate the plunger in the barrel. The tip end (55) of the plunger (54) has an axially extending wall (68) offset radially to provide a circumferentially extending space or pocket S between the sealing lip (40) and tip (55). The tip (55) is of a thickness T-3 greater than the cross sectional wall thickness T-4 of the body portion of the plunger. A downwardly and inwardly extending bottom wall (70) has raised a central indentation (72). The slanted outer-face of the bottom wall (70) preferably is disposed at a predetermined angle relative to a plane P—P through the axis A—A of the plunger so that it seats flush against the interior downwardly tapered face (62) of the barrel when the plunger is fully seated at the end of a discharge stroke as shown in FIG. 10a. A flexible sealing lip (40) is formed integrally with the plunger and in the relaxed state projects at an angle alpha ($\alpha$) of about ten degrees (10°) relative to the axis A—A of the plunger. The sealing lip (40) has an outer beveled surface ($40^a$) which engages the inner side wall of the barrel to provide good sliding movement when activating the plunger in the barrel. Similar to the previously described embodiment, the outer barrel is preferably made of propylene and the plunger is preferably made of a high-density polyethylene since the combination of these materials and the specific configuration of the sealing lip facilitates movement of the parts relative to one another and does not require the close molding tolerances to provide good sliding action.

The slightly outwardly tapered section ($52^b$) of the barrel bore ($52^c$) at the open end is preferably angularly disposed relative to the longitudinal axis A—A of the barrel at an angle beta ($\beta$) of between three and five degrees (3° and 5°) thereby defining an opening at the top of the barrel of a diameter ($D_6$) greater than the diameter ($D_5$) of the flexible lip (40) in the relaxed state to thereby allow easy assembly of the parts without damage to the flexible wiper lip. The flexible sealing lip (40) engages the rib (53) at the maximum stroke to signal the user that the parts are in the position shown in FIGS. 9a and 9b. As shown in the drawings, the wiper lip is compressed slightly when it rides in the main portion of the barrel to provide the desired light essentially single line contact with the bore of the barrel for ease of operation of the dispenser in a manner to provide an effective seal preventing blow by of the liquid product when activating the plunger to discharge product through the discharge opening.

It is noted that even know the dispenser assembly of the present invention has been shown and described in connection with dispensing medicaments for children, the dispensing assembly has many other useful applications for dispensing other types of liquid products. Further, even though the high-density polyethylene and polypropylene are the preferred combination of materials, in some applications, other dissimilar combinations of materials may be used which provide the good sliding action between the flexible wiper lip or flange and the interior wall of the barrel.

Figure 11:
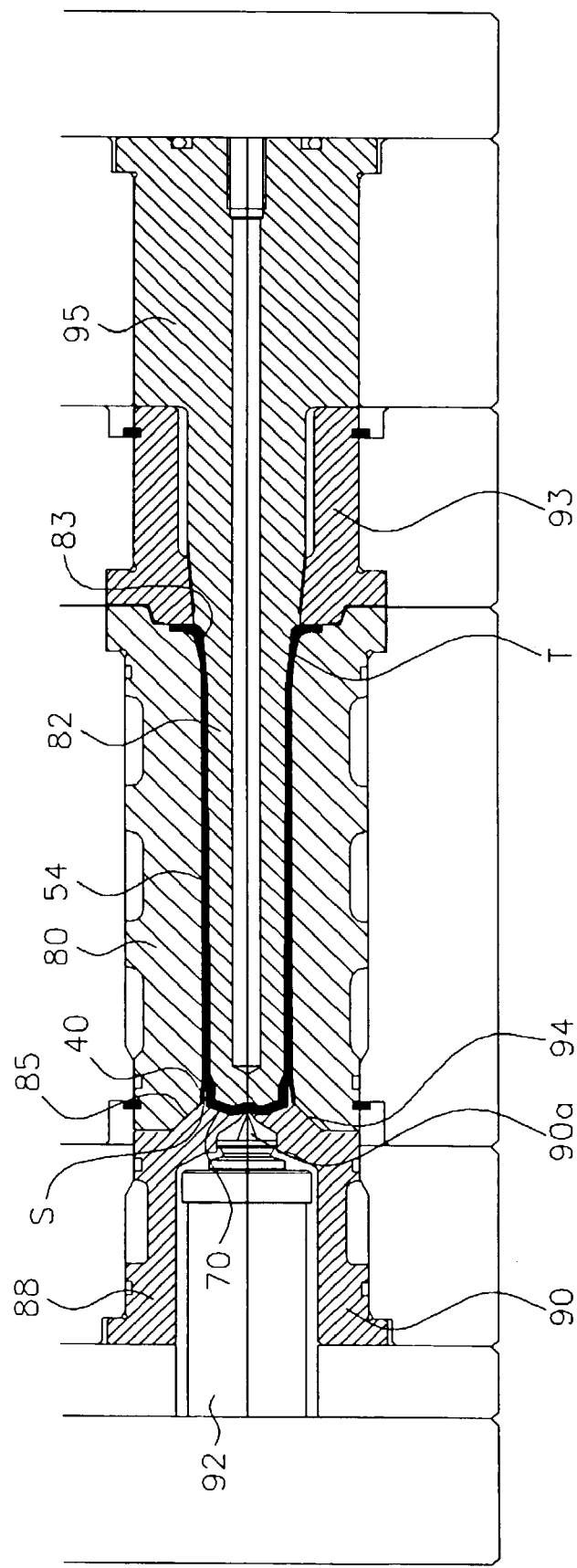
FIG. 11 is a transverse, sectional view of a molding apparatus for making a plunger for the dispenser assembly shown in FIGS. 6–10 inclusive.
Figure 12:
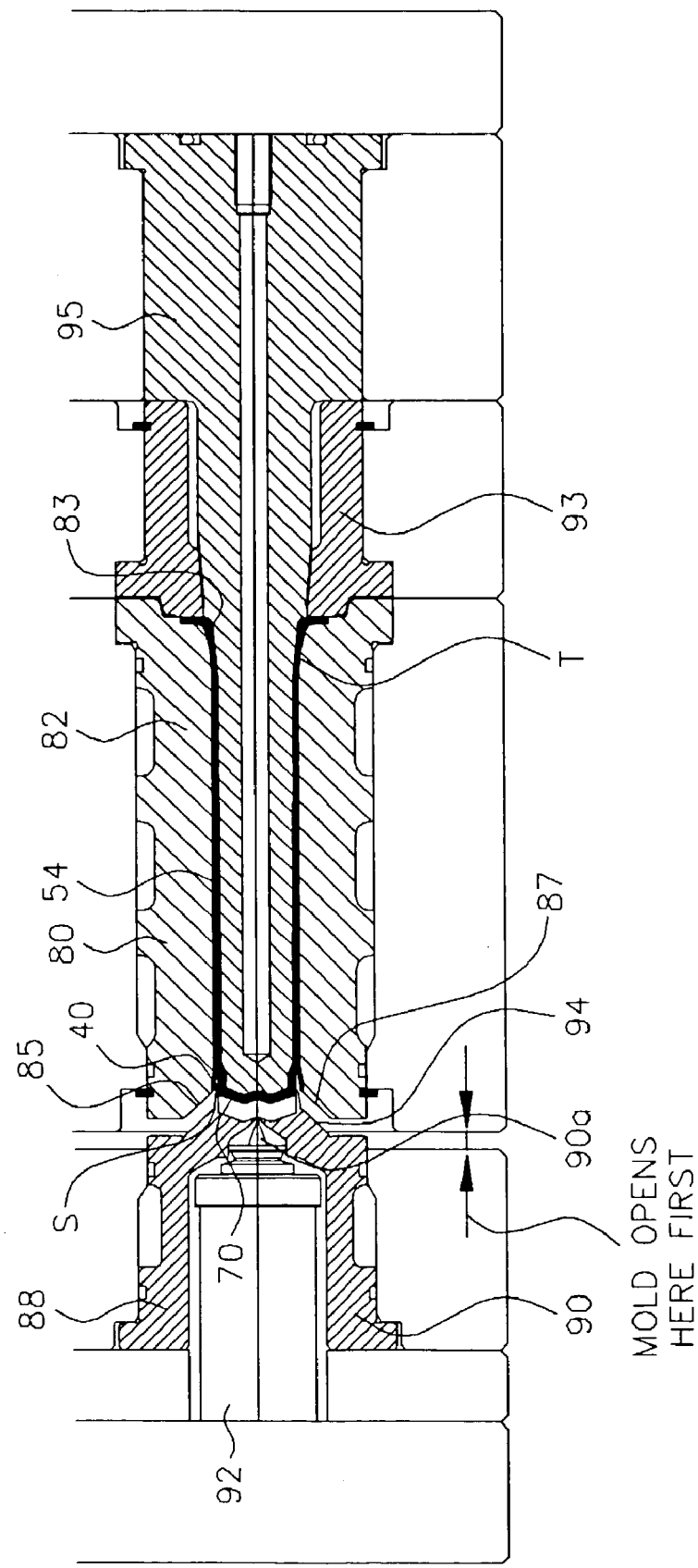
FIG. 12 is a transverse, sectional view similar to FIG. 11 showing the first stage in the plunger part removal process.
Figure 13:
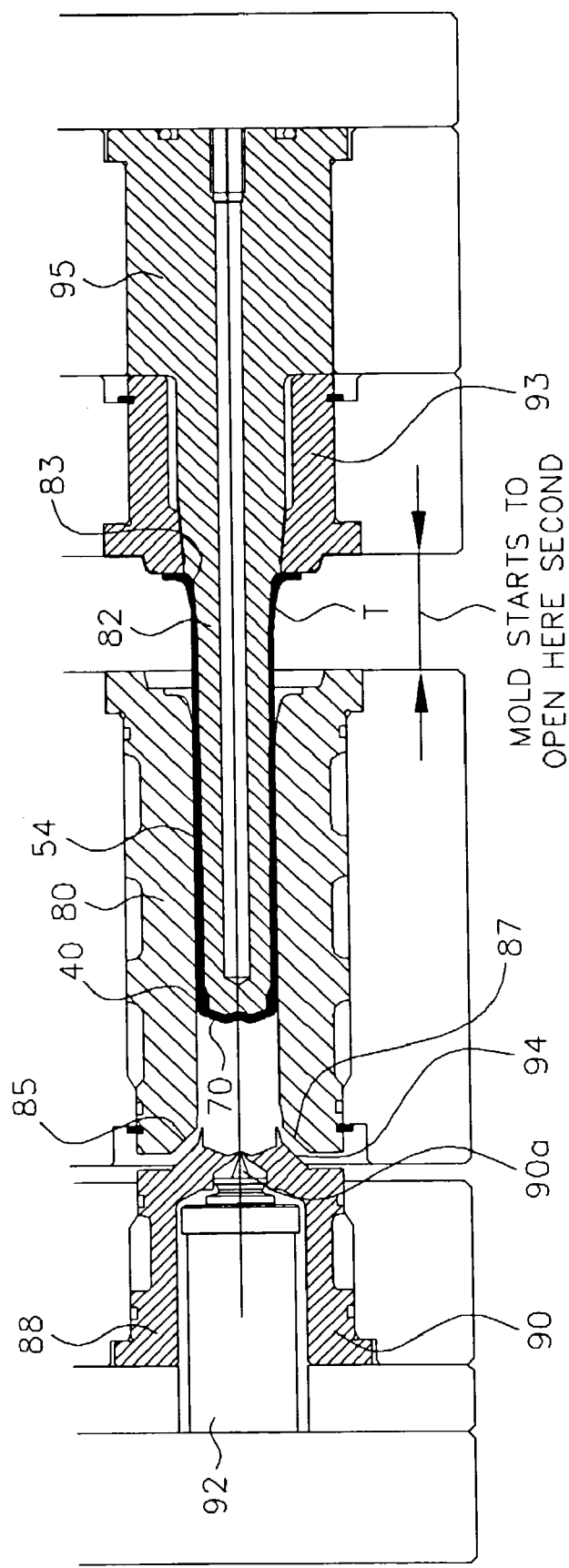
FIG. 13. Is a transverse, sectional view showing the next stage in the plunger part removal process.
Figure 14:
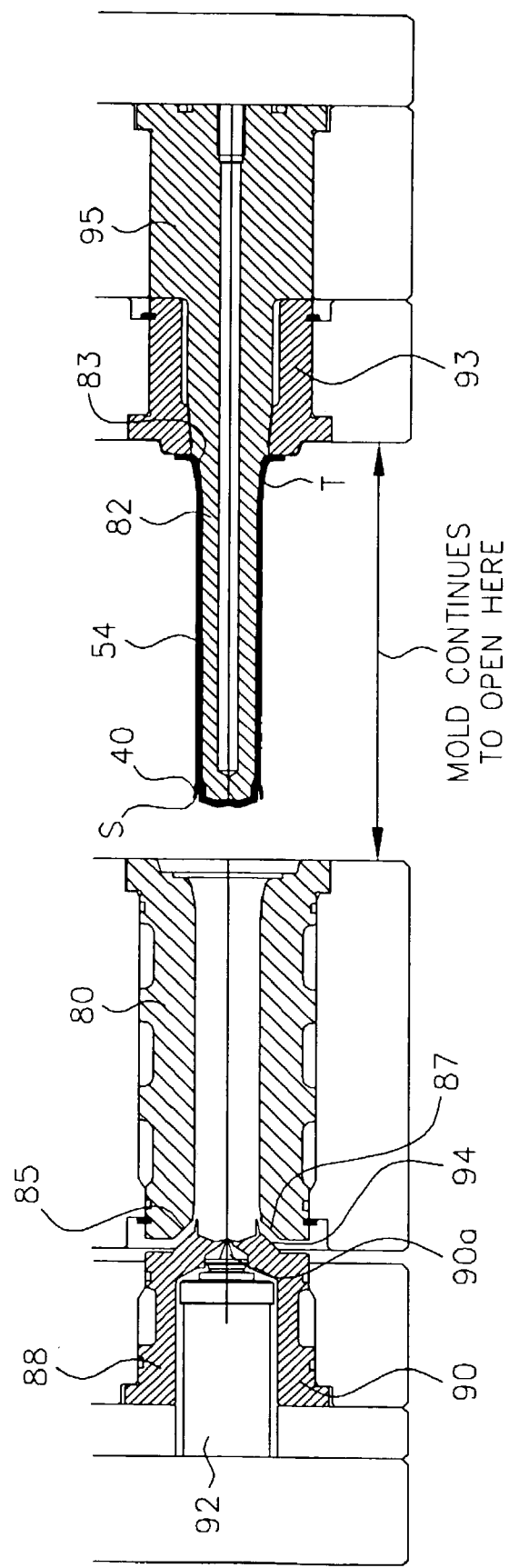
FIGS. 14–16 inclusive are transverse, sectional views showing sequentially the steps for removing the plunger part.
Figure 15:
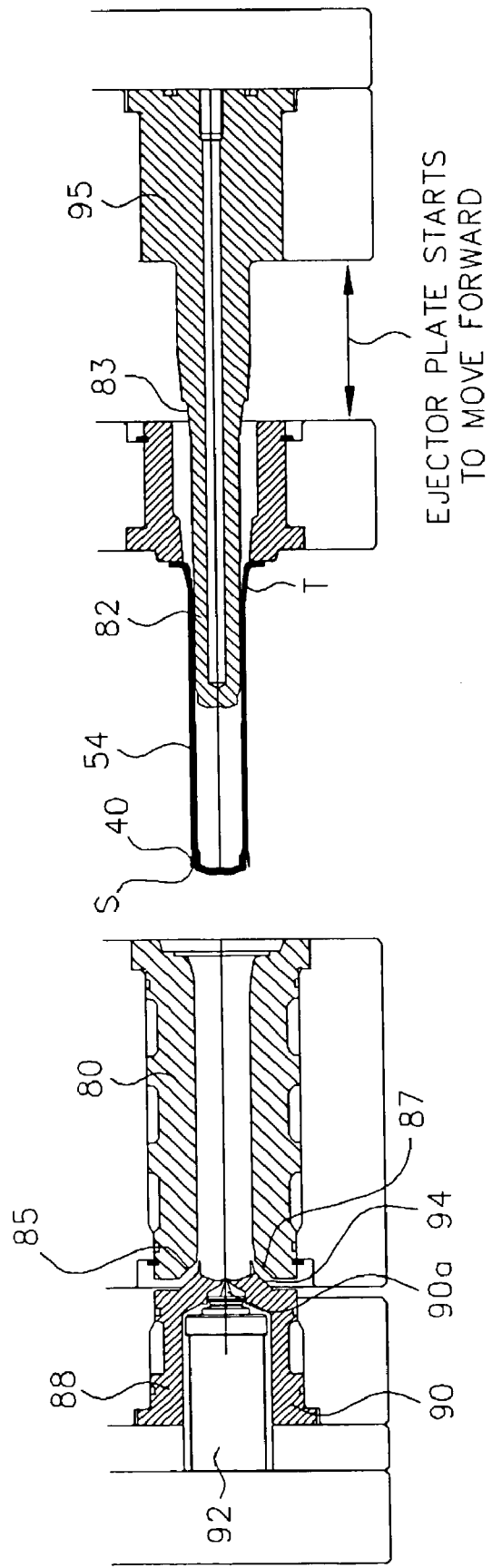
Figure 16:
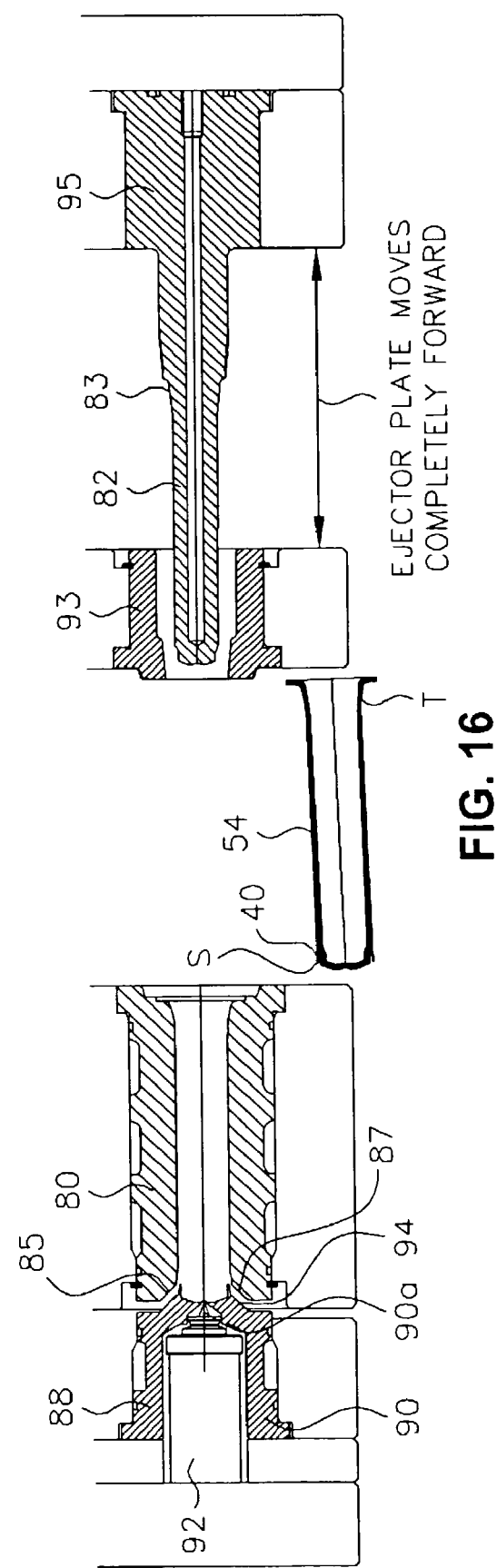
Figure 17:
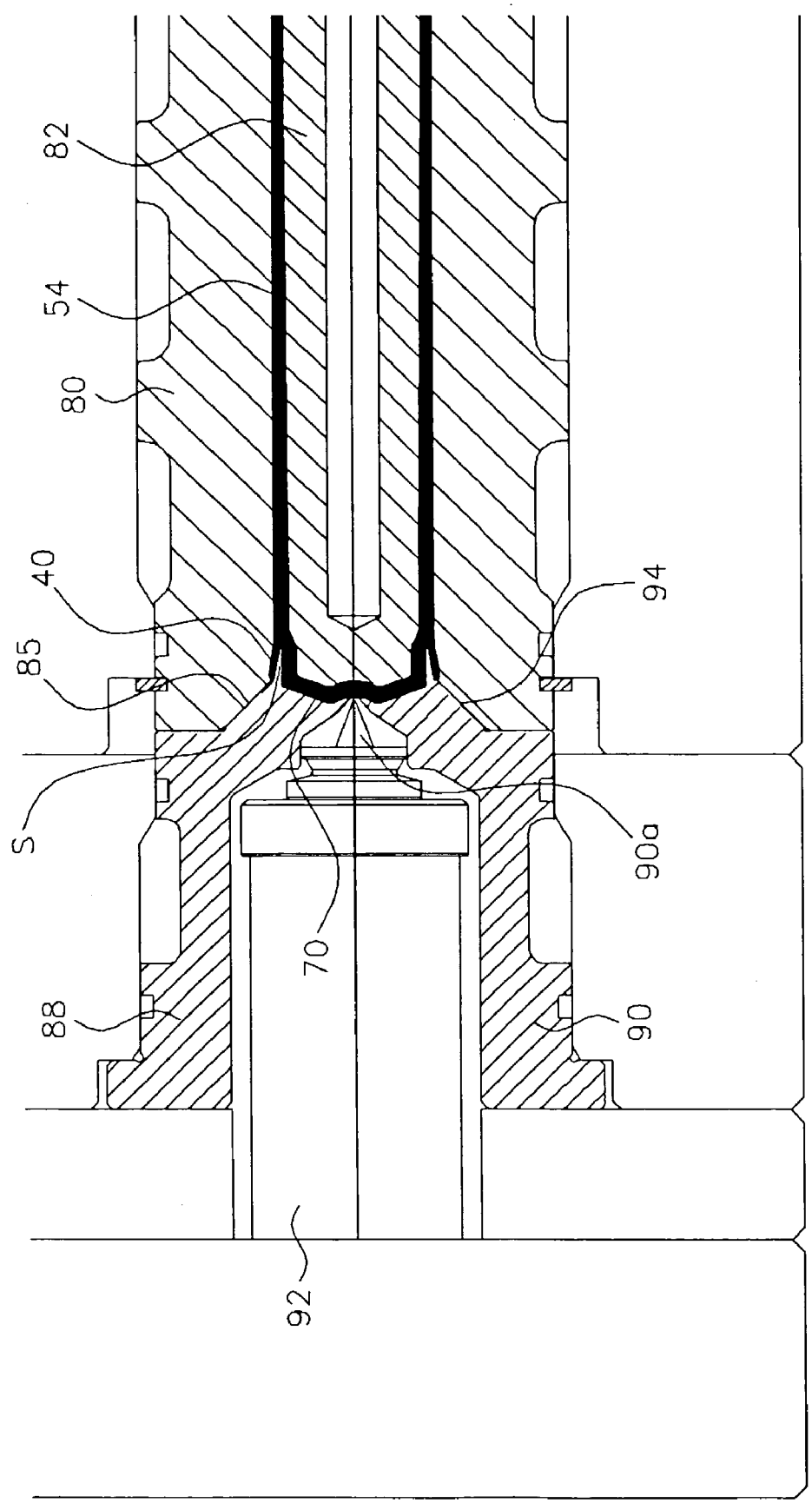
FIG. 17 is an enlarged fragmentary, transverse, sectional view of the front and rear cavity.
Figure 18:
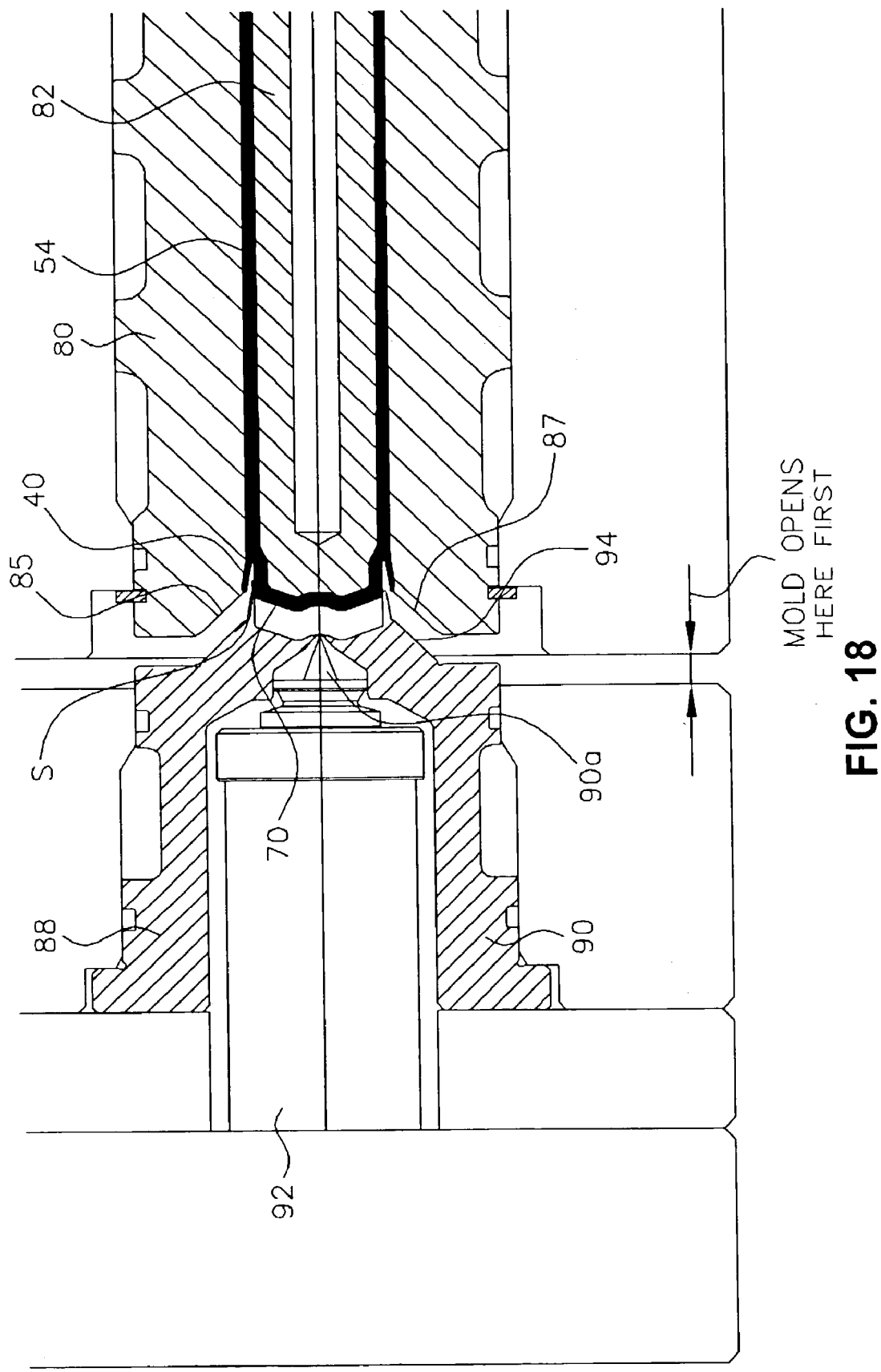
FIG. 18 is a fragmentary view similar to FIG. 12.
Figure 19:
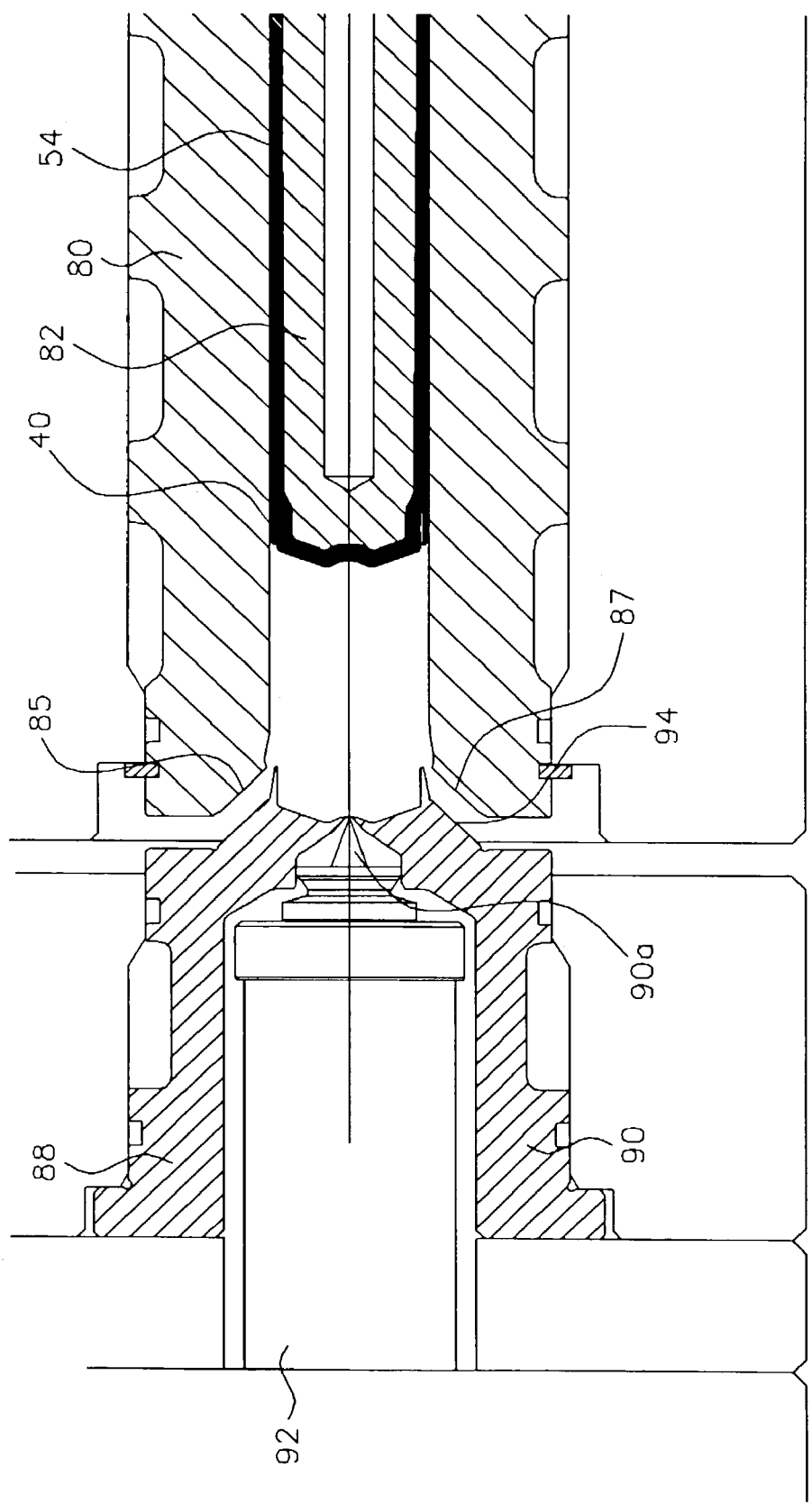
FIG. 19 is an enlarged fragmentary, sectional view showing the parts as they are in FIG. 13.

There is shown in FIGS. 11–19 inclusive a method and molding apparatus for manufacturing plungers for the dispenser assembly shown in FIGS. 6–10 inclusive. This method and apparatus are characterized by novel features of construction and arrangement facilitating easy and economical manufacture of plungers. The molding apparatus as shown in FIG. 11 comprises an elongated, tubular one-piece rear cavity (80) having an elongated generally cylindrical mold cavity (82) which is flared outwardly as to (83) adjacent one end to form the tapered bore section T of the plunger 54. The opposite end is also slightly tapered outwardly as at (85) to facilitate formation of the axially directed wiper lip (40). The molding apparatus also includes a front cavity (88) comprising a gate bushing (90) and a manifold probe (92). The gate bushing (90) is formed with a tapered front wall (94) which abuts a complementary tapered wall (87) on the front end of the rear cavity when the mold is closed. The gate bushing (90) has a circumferentially extending axially directed rim (94) which forms the circumferentially extending space or gap S between the wiper lip (40) and the tip portion (70) of the plunger (54) which permits the wiper lip (40) to be deflected radially inwardly when the finished plunger is withdrawn from the rear cavity as shown in FIG. 13. In otherwords, the diameter $D_5$ of the tip portion (70) of the plunger (54) and the cross-sectional thickness $T_w$ of the wiper lip (40) are slightly less than the outer diameter $D_o$ of the plunger to allow radially inward deflection of the wiper lip (40) when the core (95) is withdrawn in the manner shown in FIG. 13. The core (95) mounts an injector collar (93) which when actuated forwardly engages the radial flange at the outer end of the plunger (54) to strip it from the core (95) in the manner shown in FIG. 15 and FIG. 16.

Consider the operation of the molding apparatus and system described. With the mold parts in relative positions shown in FIG. 11, the gate ($90_a$) is opened to allow the plastic material to form the part in the manner shown in FIG. 11. The gate bushing (90) is then withdrawn to the position shown in FIG. 12. When the mold is opened in this fashion to break the gate, it provides the necessary clearance to allow the flexible wiper lip (40) to collapse and be withdrawn from the mold cavity. The mold starts to open at the next position (FIG. 13) allowing the plunger part (54) to start withdrawing from the cavity while the flexible wiper lip (40) collapses radially inwardly. The mold continues to open in the manner shown in FIG. 14 allowing the plunger part to completely withdraw from the cavity while the flexible wiper lip (40) expands to its normal position and provide enough clearance to eject the plunger part (See FIG. 16). The ejector plate is activated forwardly stripping the plunger part from the core at the end of the stroke the plunger part is released from the mold (See FIG. 16).

Even though particular embodiments of the present invention have been illustrated and described herein, it is not intended to limit the invention and changes and modifications may be made therein within the scope of the following claims.

What is claimed is:

1. A dispenser assembly for liquid products comprising an elongated, generally cylindrical barrel having a body portion provided with a base of a predetermined internal cross-sectional diameter and having a discharge opening at one end and open at its opposite end, an elongated, generally cylindrical hollow plunger having a tip portion and an outer diameter less than the barrel internal diameter, a circumferentially extending, axially directed flexible sealing lip adjacent the tip portion, said sealing lip having an outer diameter greater than the internal diameter of the barrel in the relaxed state, whereby the lip is flexed inwardly against its bias and providing the sole sliding contact between the plunger and barrel when the plunger and barrel are actuated axially relative to one another; the bore of said body portion having a predetermined generally uniform diameter and an outwardly flared portion adjacent the open end of said barrel, said flared portion having a maximum diameter slightly greater than the flexible sealing lip in the relaxed state, to thereby facilitate easy assembly, and a radially inwardly directed bead integrally formed with the body portion at the juncture of the bore of the body portion and flared portion, whereby when the plunger is drawn to its outer-limit position, the sealing lip engages the bead to indicate to the user not to withdraw the plunger any further.

2. A dispenser assembly as claimed in claim 1 wherein the outer peripheral edge of the flexible lip is chamfered to facilitate ease of assembly to the barrel and provide a single line contact with the bore of the barrel.

3. A dispenser assembly as claimed in claim 1 wherein the barrel and plunger are made of dissimilar materials to provide a degree of lubricity contributing to the ease of the movement of the plunger in the bore of the barrel.

* * * * *